United States Patent
Garst et al.

(10) Patent No.: US 8,524,671 B2
(45) Date of Patent: Sep. 3, 2013

(54) CYCLOSPORIN DERIVATIVES FOR TREATING INFLAMMATORY DISEASES AND CONDITIONS

(75) Inventors: Michael E. Garst, Newport Beach, CA (US); Michael E. Stern, Mission Viejo, CA (US)

(73) Assignee: Allergan, Inc, Irvine, CA (US)

( * ) Notice: Subject to any disclaimer, the term of this patent is extended or adjusted under 35 U.S.C. 154(b) by 381 days.

(21) Appl. No.: 12/785,133

(22) Filed: May 21, 2010

(65) Prior Publication Data

US 2010/0305037 A1    Dec. 2, 2010

Related U.S. Application Data

(60) Provisional application No. 61/181,382, filed on May 27, 2009.

(51) Int. Cl.
A61K 38/13 (2006.01)

(52) U.S. Cl.
USPC .......................................................... 514/20.5

(58) Field of Classification Search
USPC .......................................................... 514/20.5
See application file for complete search history.

(56) References Cited

U.S. PATENT DOCUMENTS

| | | | |
|---|---|---|---|
| 5,944,299 A | 8/1999 | Toyama | |
| 5,948,755 A | 9/1999 | Barriere et al. | |
| 5,965,527 A | 10/1999 | Barriere et al. | |
| 5,977,067 A | 11/1999 | Evers et al. | |
| 6,254,860 B1 | 7/2001 | Garst | |
| 6,346,511 B1 | 2/2002 | Singh et al. | |
| 6,350,442 B2 * | 2/2002 | Garst | 424/78.04 |
| 6,583,265 B1 * | 6/2003 | Ellmerer-Muller et al. | 530/317 |
| 2005/0059583 A1 | 3/2005 | Acheampong et al. | |

FOREIGN PATENT DOCUMENTS

| | | |
|---|---|---|
| EP | 0194972 | 9/1986 |
| WO | 98-28328 | 7/1998 |
| WO | 98-28329 | 7/1998 |
| WO | 98-28330 | 7/1998 |
| WO | 99-32512 | 7/1999 |
| WO | 99-67280 | 12/1999 |
| WO | 00-61168 | 10/2000 |
| WO | 2010-006117 | 1/2010 |

OTHER PUBLICATIONS

Immunosuppressive in Wikipedia, 2012.*

* cited by examiner

*Primary Examiner* — Yong Chu
(74) *Attorney, Agent, or Firm* — Joel B. German; Debra D. Condino

(57) ABSTRACT

The present invention provides a method for the treatment of inflammatory diseases and/or conditions, e.g. allergic conjunctivitis, uveitis or phacoanaphylactic endophthalmitis in an eye of a mammal, said method comprising administering to said mammal in need of treatment a therapeutically effective amount of a novel cyclosporin A derivative selected from the group consisting of compounds represented by the formula:

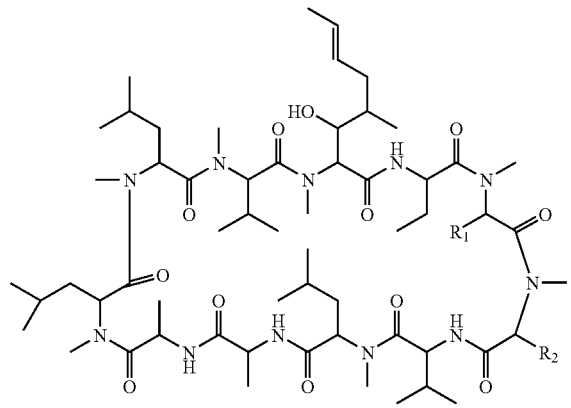

wherein $R_1$ is S-Alk-R wherein Alk is an alkylene linkage, preferably a methylene or poly methylene linkage, or a polyalkenylene linkage, e.g. a $C_3$ to $C_6$ alkenylenyl linkage and R is a hydrogen or a unsubstituted or substituted hydrocarbyl group.

9 Claims, No Drawings

CYCLOSPORIN DERIVATIVES FOR TREATING INFLAMMATORY DISEASES AND CONDITIONS

CROSS-REFERENCE

This application claims the benefit of U.S. Provisional Patent Application Ser. No. 61/181,382, filed on May 27, 2009, the entire disclosure of which is incorporated herein by this specific reference.

BACKGROUND OF THE INVENTION

1. Field of the Invention

The invention relates to a method of treating inflammatory, including ocular and/or dermal, diseases and conditions having inflammation as a component of such ocular and/or dermal diseases and conditions, with cyclosporine derivatives. In particular, the present invention relates to a method for the treatment of allergic conjunctivitis, aqueous deficient dry-eye state, phacoanaphylaxis endophthalmitis and uveitis using certain novel cyclosporine derivatives.

2. Description of the Related Art

Inflammation is the complex biological response of vascular tissues to harmful stimuli, such as pathogens, damaged cells, or irritants. It is a protective attempt by the organism to remove the injurious stimuli as well as initiate the healing process for the tissue.

In the absence of inflammation, wounds and infections would never heal and progressive destruction of the tissue would compromise the survival of the organism. However, inflammation which runs unchecked can also lead to a host of diseases, such as hay fever, atherosclerosis, and rheumatoid arthritis. It is for this reason that inflammation is normally tightly regulated by the body.

Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

Acute inflammation is a short-term process which is characterized by the classic signs of inflammation—swelling, redness, pain, heat, and loss of function—due to the infiltration of the tissues by plasma and leukocytes. It occurs as long as the injurious stimulus is present and ceases once the stimulus has been removed, broken down, or walled off by scarring.

The process of acute inflammation is initiated by the blood vessels local to the injured tissue, which alter to allow the exudation of plasma proteins and leukocytes into the surrounding tissue. The increased flow of fluid into the tissue causes the characteristic swelling associated with inflammation since the lymphatic system doesn't have the capacity to compensate for it, and the increased blood flow to the area causes the reddened color and increased heat. The blood vessels also alter to permit the extravagation of leukocytes through the endothelium and basement membrane constituting the blood vessel. Once in the tissue, the cells migrate along a chemotactic gradient to reach the site of injury, where they can attempt to remove the stimulus and repair the tissue.

Meanwhile, several biochemical cascade systems, consisting of chemicals known as plasma-derived inflammatory mediators, act in parallel to propagate and mature the inflammatory response. These include the complement system, coagulation system and fibrinolysis system.

Finally, down-regulation of the inflammatory response concludes acute inflammation. Removal of the injurious stimuli halts the response of the inflammatory mechanisms, which require constant stimulation to propagate the process. Additionally, many inflammatory mediators have short half lives and are quickly degraded in the tissue, helping to quickly cease the inflammatory response once the stimulus has been removed.

Chronic inflammation is a pathological condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis.

Endogenous causes include persistent acute inflammation. Exogenous causes are varied and include bacterial infection, prolonged exposure to chemical agents such as silica, tobacco smoke, or autoimmune reactions such as rheumatoid arthritis.

In acute inflammation, removal of the stimulus halts the recruitment of monocytes (which become macrophages under appropriate activation) into the inflamed tissue, and existing macrophages exit the tissue via lymphatics. However in chronically inflamed tissue the stimulus is persistent, and therefore recruitment of monocytes is maintained, existing macrophages are tethered in place, and proliferation of macrophages is stimulated.

The exudative component involves the movement of plasma fluid, containing important proteins such as fibrin and immunoglobulins (antibodies), into inflamed tissue. This movement is achieved by the chemically-induced dilation and increased permeability of blood vessels, which results in a net loss of blood plasma. The increased collection of fluid into the tissue causes edema.

Acute inflammation is characterised by marked vascular changes, including vasodilation, increased permeability, and the slowing of blood flow, which are induced by the actions of various inflammatory mediators. Vasodilation occurs first at the arteriole level, progressing to the capillary level, and brings about a net increase in the amount of blood present, causing the redness and heat of inflammation. Increased permeability of the vessels results in the movement of plasma into the tissues, with resultant stasis due to the increase in the concentration of the cells within blood—a condition characterized by enlarged vessels packed with cells. Stasis allows leukocytes to marginate along the endothelium, a process critical to their recruitment into the tissues. Normal flowing blood prevents this, as the shearing force along the periphery of the vessels moves cells in the blood into the middle of the vessel.

Abnormalities associated with inflammation comprise a large, unrelated group of disorders which underly a variety of human diseases. The immune system is often involved with inflammatory disorders, demonstrated in both allergic reactions and some myopathies, with many immune system disorders resulting in abnormal inflammation. Non-immune diseases with aetiological origins in inflammatory processes are thought to include cancer, atherosclerosis, and ischemic heart disease.

A large variety of proteins are involved in inflammation, and any one of them is open to a genetic mutation which impairs or otherwise deregulates the normal function and expression of that protein.

Examples of disorders associated with inflammation include:

Asthma
Autoimmune diseases
Chronic inflammation
Chronic prostatitis
Glomerulonephritis
Hypersensitivities
Inflammatory bowel diseases
Pelvic inflammatory disease
Reperfusion injury
Rheumatoid arthritis
Transplant rejection
Vasculitis.

The inflammatory response must be actively terminated when no longer needed to prevent unnecessary damage to tissues. Failure to do so results in chronic inflammation, cellular destruction, and attempts to heal the inflamed tissue. One intrinsic mechanism employed to terminate inflammation is the short half-life of inflammatory mediators in vivo. They have a limited time frame to affect their target before breaking down into non-functional components, therefore constant inflammatory stimulation is needed to propagate their effects.

Active mechanisms which serve to terminate inflammation include

TGF-β from macrophages
Anti-inflammatory lipoxins
Inhibition of pro-inflammatory molecules, such as leukotrienes.

Specific diseases and conditions of the eye having an inflammatory component include allergic conjunctivitis, phacoanaphylactic endophthalmitis and uveitis. These diseases and conditions can be located throughout the eye, in both the posterior and anterior chambers of the eye as well as in the vitreous body.

Uveitis, the inflammation of the uvea, is responsible for about 10% of the visual impairment in the United States. Phacoanaphylactic endophthalmitis is a human autoimmune disease.

Panuveitis refers to inflammation of the entire uveal (vascular) layer of the eye. Posterior uveitis generally refers to chorioretinitis, and anterior uveitis refers to iridocyclitis. The inflammatory products (i.e. cells, fibrins, excess proteins) of these inflammations are commonly found in the fluid spaces if the eye, i.e. anterior chamber, posterior chamber and vitreous space as well as infiltrating the tissue intimately involved in the inflammatory response. Uveitis may occur following surgical or traumatic injury to the eye; as a component of an autoimmune disorder, i.e. rheumatoid arthritis, Behcet's disease, ankylosing spondylitis, sarcoidosis; as an isolated immune mediated ocular disorder, i.e. pars planitis, iridocyclitis etc., unassociated with known etiologies; and following certain systemic diseases which cause antibody-antigen complexes to be deposited in the uveal tissues. Together these disorders represent the non-infectious uveitis.

Cyclosporins have been used to treat inflammatory conditions including an autoimmune component such as arthritis (for example rheumatoid arthritis, arthritis chronica progrediente and arthritis deformans) and rheumatic diseases. Specific auto-immune diseases for which Cyclosporin has been proposed or applied include, autoimmune hematological disorder (including e.g. hemolytic anaemia, aplastic anaemia, pure red cell anaemia and idiopathic thrombocytopaenia), systemic lupus erythematosus, poly-chondritis, scleroderma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary biliary cirrhosis, juvenile diabetes (diabetes mellitus type 1), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy). (See U.S. Pat. No. 6,346,511.)

Thus, it will be understood that it is desirable to develop compounds that are useful in treating inflammatory diseases and conditions. It has been found that the compounds disclosed herein may be used to treat various inflammatory diseases and conditions.

Such compounds include the methylthio-substituted cyclosporin A and other alkylthio-substituted cyclosporin A derivatives described in PCT application Nos. 98-379455, 98-379456 and 98-379457, which have been found to be active against certain retroviruses, especially AIDS (acquired immunodeficiency syndrome) and ARC (AIDS-related complex) when administered orally, parenterally, rectally or by inhalation. In addition, these compounds have generally been found to have only a very weak immunosuppressant action, and to show anti-retroviral activity at non-cytotoxic and non-cytostatic concentrations. These compounds are claimed to have a synergistic action with other agents active against retrovirus (such as inhibitors of reverse transcriptase, protease, integrase, HIV replication and nucleocapside). (See also U.S. Pat. Nos. 5,944,299; 5,977,067; 5,965,527 and 5,948,755).

These compounds are also claimed for use in the treatment of ocular diseases and conditions in U.S. Pat. Nos. 6,350,442 and 6,254,860.

Thus, it is one object of this invention to treat inflammatory diseases and conditions, including diseases and conditions having inflammation as a component thereof, with cyclosporine derivatives.

It is another object of this invention to provide cyclosporine A derivatives to treat ocular diseases and conditions, such as allergic conjunctivitis.

It is one object of this invention to treat ocular diseases and conditions, including ocular diseases and conditions having inflammation as a component thereof, with cyclosporine derivatives.

It is another object of the invention to treat dermal diseases and conditions, including dermal diseases and conditions having inflammation as a component thereof, with cyclosporine derivatives.

It is another object of the invention to treat dermal conditions, such as psoriasis and dermatitis.

Other objects of this invention will become apparent from a reading of the present specification.

SUMMARY OF THE INVENTION

The present invention provides a method for treating an inflammatory disease, disorder or condition of a mammal, e.g. a human, such as an inflammatory disease, disorder or condition of the eye, for example, allergic conjunctivitis, uveitis, or phacoanaphylactic endophthalmitis, comprising the step of administering to a patient in need thereof, including topically or systemically administering to the eye of such patient, a therapeutically effective amount of a compound selected from the group consisting of cyclosporin A derivatives of the formula described below. The present invention preferably provides a method for treating a disorder or condition of the eye, with a therapeutically effective amount of a compound selected from the group consisting of cyclosporin A derivatives. The cyclosporin A derivatives utilized in the method(s) of the present invention are represented by the formula

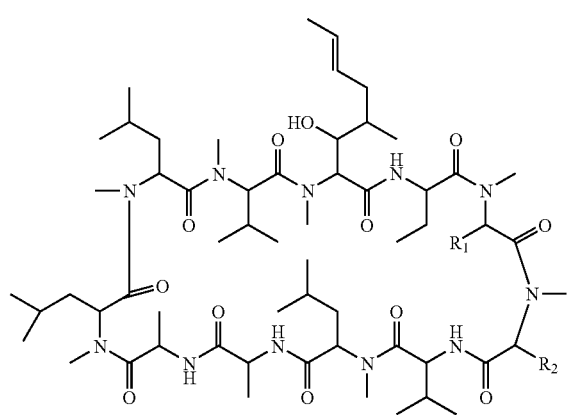

wherein $R_1$ is S-Alk-R wherein Alk is an alkylene linkage, preferably a methylene or poly methylene linkage, e.g. a $C_2$ to $C_6$ polymethylene linkage, or a polyalkenylene linkage, e.g. a $C_3$ to $C_6$ alkenylenyl linkage, and R is hydrogen or a unsubstituted or substituted hydrocarbyl group. Preferably, R is a nitrogen-containing hydrocarbyl group, e.g. a poly nitrogen-containing hydrocarbyl group, having 2 or 3 nitrogen atoms, i.e. an amidine or guanidine-containing hydrocarbyl radical. In particular, R may be selected from the group consisting of radicals of the following formulae: R is $-N=C(NR_3R_4)(NR_5R_6)$ or $-NR_7-[(NR_3R_4)C=NR_5]$, i.e. guanidines or $-N=C(R_8)(NR_9R_{10})$, i.e. amidines, wherein $R_3$-$R_{10}$ is H, Alk, Ar or $(CH_2)nAr$ wherein Ar is an aryl group and n is an integer of from 1 to 13 or $R_3$ and $R_4$, or $R_4$ and $R_5$, or $R_5$ and $R_7$, or $R_3$ and $R_7$, or $R_9$ and $R_{10}$, or $R_8$ and $R_9$, together, may be $-(CH_2)_x-$, wherein x is an integer of from 2 to 5, e.g. $CH_2-CH_2-$ or $-CH_2-CH_2-CH_2-$.

$R_2$ may be selected from the group consisting of hydroxyl, lower alkyl and hydroxyl-substituted lower alkyl.

For example, $R_1$ may be $-S(CH_2)_2N=C(NH_2)_2$ and $R_2$ may be $-CH_2CH(CH_3)_2$, $-CH_2C(OH)(CH_3)_2$, $-CH(CH_3)_2$ or $-CH(CH_3)CH_2CH_3$.

DETAILED DESCRIPTION OF THE INVENTION

The present invention provides a method for the treatment of inflammatory diseases and conditions, including diseases and conditions of the eye, having an inflammatory component associated therewith, e.g. by topical application to the affected eye, of a cyclosporin derivative, represented by the formula below

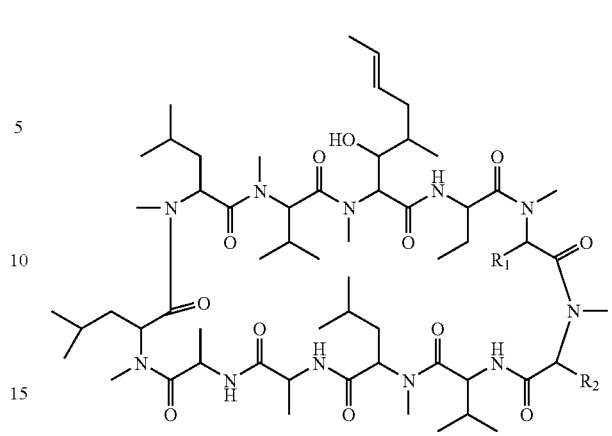

wherein $R_1$ and $R_2$ are defined above. In particular $R_1$ is S-Alk-R wherein Alk is an alkylene linkage, preferably a methylene or poly methylene linkage, e.g. a $C_2$ to $C_6$ polymethylene linkage, or a polyalkenylene linkage, e.g. a $C_3$ to $C_6$ alkenylenyl linkage and $R_2$ is selected from the group consisting of hydroxyl, lower alkyl and hydroxyl substituted lower alkyl.

In a first aspect of the invention, R is $-N=C(NR_3R_4)(NR_5R_6)$ or $-NR_7[(NR_3R_4)C=NR_5]$, i.e. a guanidine or $-N=C(R_8)(NR_9R_{10})$, i.e. an amidine wherein $R_3$-$R_{10}$ is H, Alk, Ar or $(CH_2)nAr$ wherein Ar is an aryl group and n is an integer of from 1 to 13 or $R_3$ and $R_4$, or $R_4$ and $R_5$, or $R_5$ and $R_7$, or $R_3$ and $R_7$, or $R_9$ and $R_{10}$, or $R_8$ and $R_9$, together, may be $-(CH_2)_x-$, wherein x is an integer of from 2 to 5, e.g. $-CH_2-CH_2-$ or $-CH_2-CH_2-CH_2-$.

In a second aspect of the invention, $R_1$ is a hydrogen atom or a radical of formula (Ia):

in which
Alk-$R_{11}$ represents a methyl radical, or alternatively
Alk represents a $C_2$-$C_6$ straight chain or branched alkylene radical or a $C_3$-$C_6$ cycloalkylene radical, and
$R_{11}$ represents
a hydrogen atom or a hydroxyl, carboxyl or alkyloxycarbonyl radical, or
an $-NR_{12}R_{13}$ radical in which $R_{12}$ and $R_{13}$, which are identical or different, represent a hydrogen atom or a phenyl, alkyl, $C_2$-$C_4$ alkenyl or $C_3$-$C_6$ cycloalkyl radical, said radical optionally substituted with selected from a halogen atom, an alkyloxy, alkyloxycarbonyl, amino, alkylamino and dialkylamino radical; or
$R_{12}$ and $R_{13}$ represent a benzyl or saturated or unsaturated heterocyclic radical, said heterocyclic radical containing from 5 to 6 ring members and from 1 to 3 heteroatoms;
or in which $R_{12}$ and $R_{13}$ form, together with the nitrogen atom to which they are attached, a saturated or unsaturated 4- to 6-membered heterocycle, which heterocycle having an additional heteroatom selected from nitrogen, oxygen and sulphur, and wherein said saturated or unsaturated heterocycle is optionally substituted by an alkyl, phenyl or benzyl radical, or $R_1$ is a radical of the formula (Ib): $-N(R_{14})-(CH_2)_n-NR_{12}R_{13}$ in which $R_{12}$ and $R_{13}$ are as defined above, $R_{14}$ represents a hydrogen atom or an alkyl radical and n is an integer ranging from 2 to 4,
and $R_2$ is selected from the group consisting of hydroxyl, lower alkyl and hydroxyl substituted lower alkyl, with the proviso that, when $R_1$ is a hydrogen atom, then $R_2$ is not an alkyl butyl radical, and wherein the alkyl portions or radicals defined above are straight chain or branched and contain from 1 to 4 carbon atoms, or a pharmaceutically acceptable salt thereof.

In the cyclosporine A derivatives of this second aspect of the invention, the trans butene moiety, which is normally present in the 1-position of cyclosporine A, may be replaced with $R_{15}$ wherein $R_{15}$ represents a radical of formula —$CH_2CHCHCH_2$—$R_{16}$ (Ic) or —$CH_2SR_{17}$ (Id), wherein $R_{16}$ represents an alkylthio, aminoalkylthio, alkylaminoalkylthio, dialkylaminoalkylthio, pyrimidinylthio, thiazolylthio, N-alkylimidazolylthio, hydroxyalkylphenylthio, hydroxyalkylphenyloxy, nitrophenylamino or 2-oxopyrimidin-1-yl radical and $R_{17}$ represents an alkyl radical.

This invention also provides pharmaceutical compositions for topical application in the treatment of an inflammatory disease, disorder or condition of a mammal, e.g. a human, such as an inflammatory disease, disorder or condition of the eye, for example, allergic conjunctivitis, uveitis, or phacoanaphylactic endophthalmitis, comprising the step of administering to a patient in need thereof, including topically or systemically administering to the eye of such patient, a therapeutically effective amount of a compound selected from the group consisting of the above cyclosporin A derivatives.

For the purpose of describing and claiming the present invention the following terms shall have the following meanings:

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino and SH.

"Alkenyl" refers to a straight-chain, branched or cyclic unsaturated hydrocarbon group containing at least one carbon-carbon double bond. Preferably, the alkenyl group has 2 to 12 carbons. More preferably it is a lower alkenyl of from 2 to 7 carbons, most preferably 2 to 4 carbons. The alkenyl group may be optionally substituted with one or more substituents selected from the group consisting of hydroxyl, cyano, alkoxy, O, S, $NO_2$, halogen, dimethyl amino and SH.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Alkoxy" refers to an "O-alkyl" group.

"tBoc" refers to a t-butyloxycarbonyl protecting group.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen.

The cyclosporine A derivatives used in the method of this invention are prepared as follows:

Compounds where $R_4$, $R_5$ and $R_6$ are hydrogen and $R_7$ is hydrogen, alkyl, substituted alkyl or aryl may be prepared by reaction of a compound of formula (I) where X is a leaving group and P is a protecting group with a compound of formula (II) in a suitable solvent such as methanol to afford compounds of formula (III). For compounds of formula I, typical examples of the protecting group are where X=chlorine, MeS, MeSO2, 1-imidazolyl and especially 1-pyrazolyl. Protecting groups P are preferably tertiary butyloxycarbonyl groups (tBoc) groups.

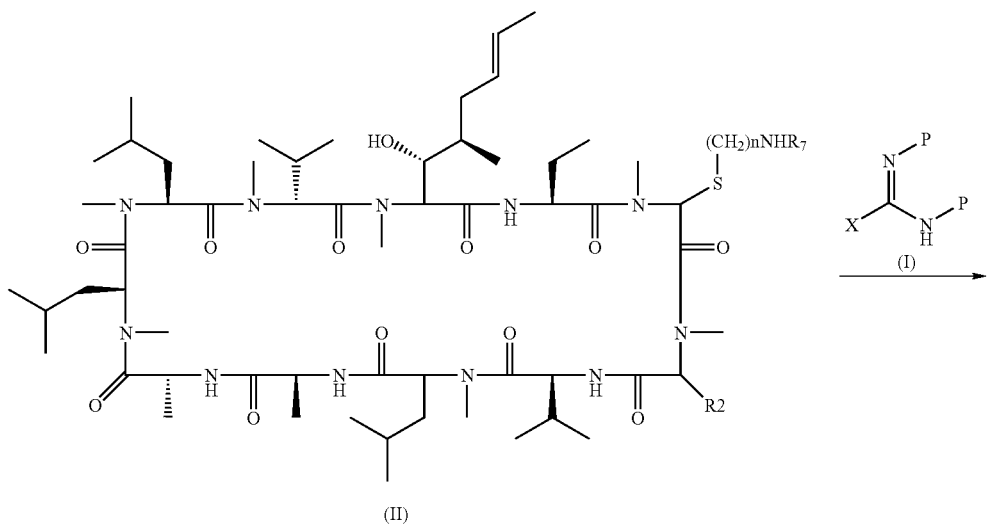

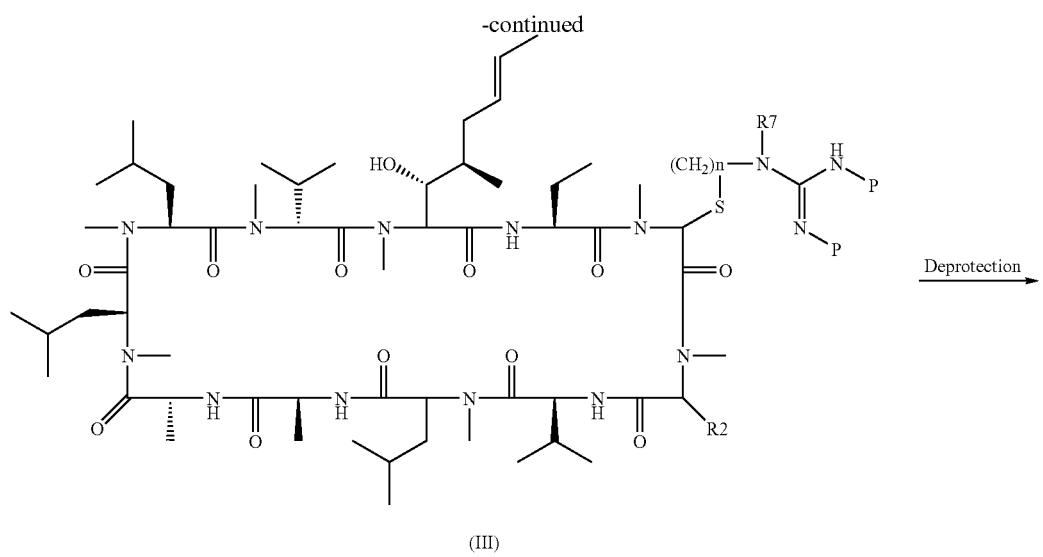

(III)

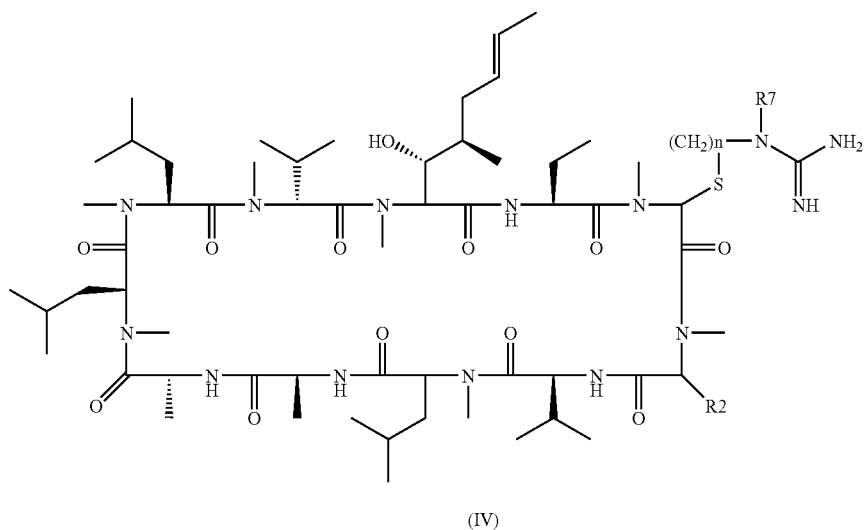

(IV)

Compounds of formula (III) may be de-protected under a variety of conditions to provide compounds of formula (IV). For example, when P=tertiary butyloxycarbonyl groups (tBoc), this may be removed under acidic conditions using acids such as methanesulphonic acid.

Compounds of formula (V) where $R_7$ is hydrogen, alkyl, substituted alkyl or aryl; $R_3$ is alkyl, substituted alkyl or aryl, may be prepared by reaction of a compound of formula (VI) where X is a leaving group and P is a protecting group with a compound of formula (II) in a suitable solvent such as methanol to afford compounds of formula (VII).

For compounds of formula (VI), typical examples of the protecting group are where X=chlorine, MeS, MeSO2, 1-imidazolyl and especially 1-pyrazolyl. Protecting groups P are preferably tertiary butyloxycarbonyl groups (tBoc) groups.

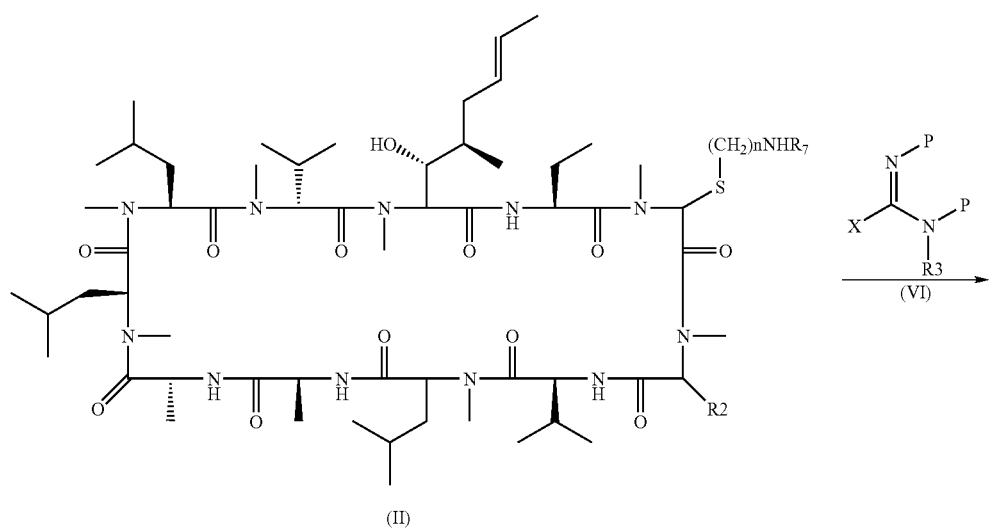
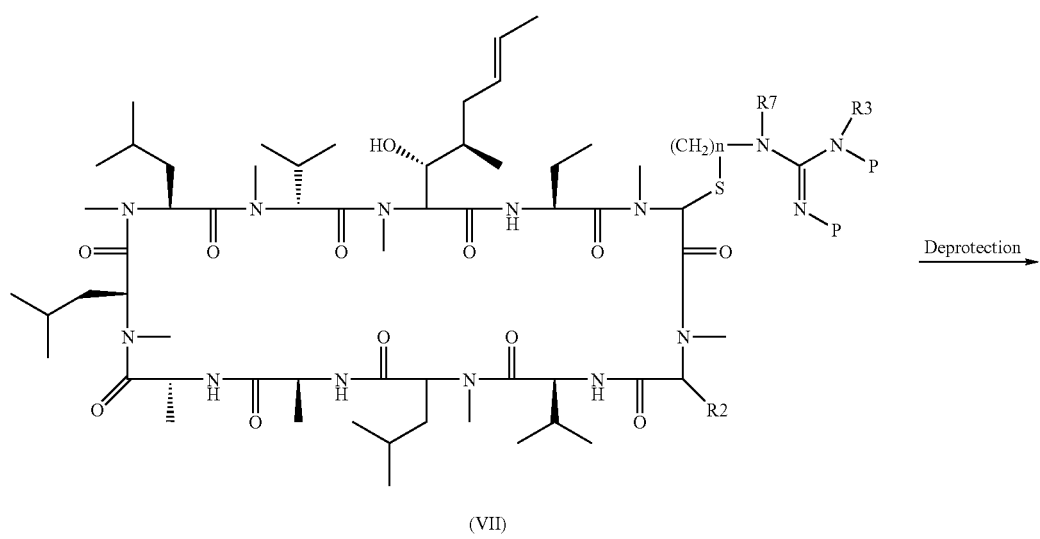
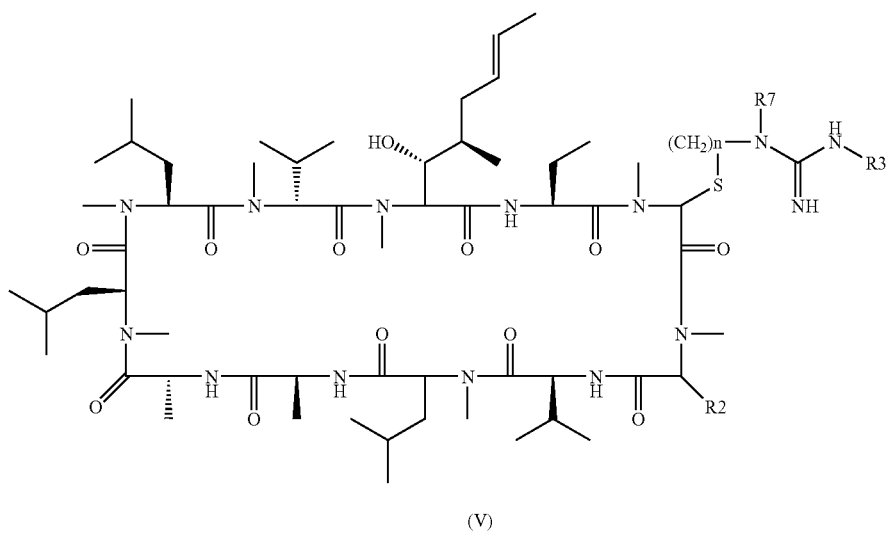

For example, in WO/2003/051797N,N'-Di-tBoc-N-methyl-1H-pyrazole-1-carboxamidine has been used to prepare an N-methyl guanidine in an unrelated chemical family.

Other compounds of the invention may be made in similar ways using related synthetic methods with, if appropriate, suitable protecting groups compatible with the synthetic methodology.

Compounds of formula (X) where R is —N=C($R_8$)—$NR_9R_{10}$ (amidines) where $R_8$ is hydrogen, alkyl, substituted alkyl or aryl and $R_9$ and $R_{10}$ can be alkyl, substituted alkyl or aryl or $R_9$ and $R_{10}$ can form a ring may be prepared by reaction of a compound of formula (VIII) with a compound of formula (IX) to afford compounds of formula (X).

$R_{11}$ is preferably lower alkyl and typical examples of compound (VIII) are Dimethylformamide dimethylacetal (DMF.DMA) and Dimethylacetamide dimethylacetal (DMA.DMA).

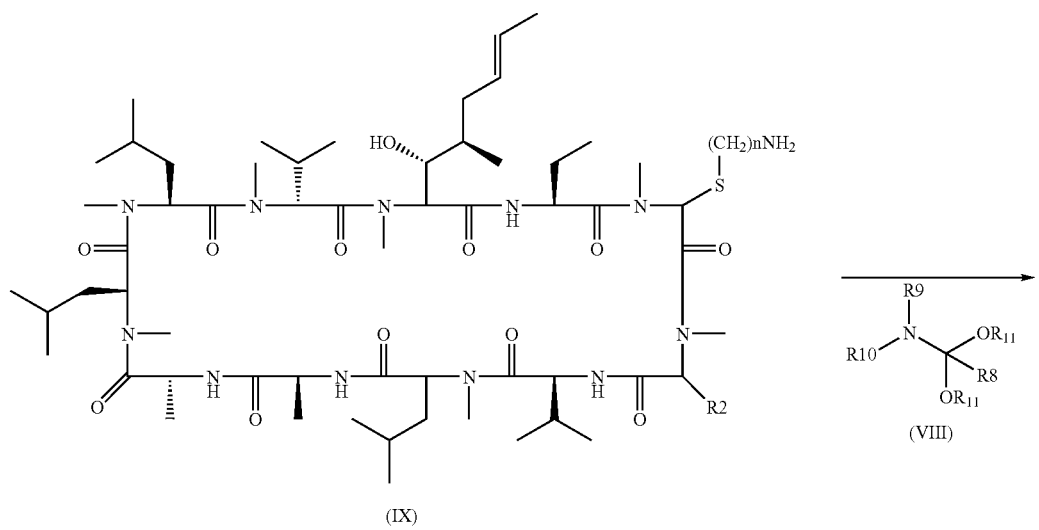

(IX)

(VIII)

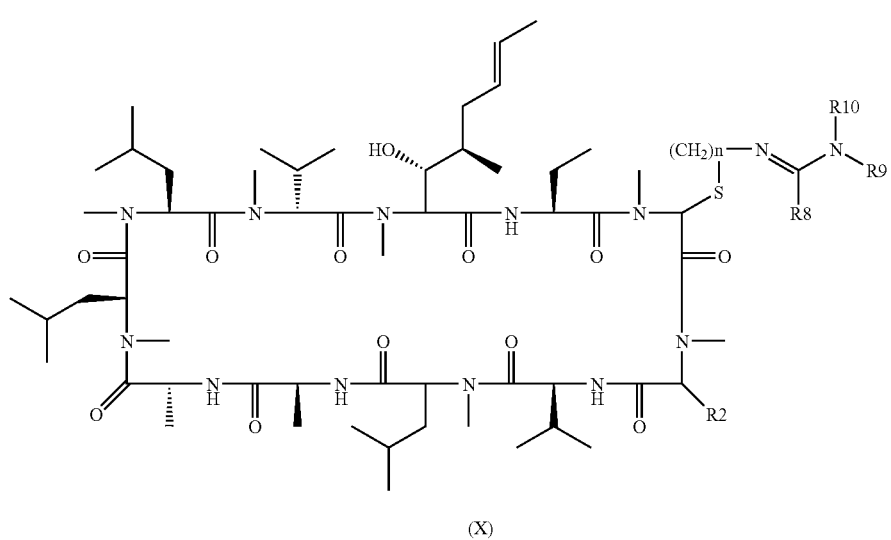

(X)

Below are specific examples of the preparation of certain compounds of the invention by the above general procedures.

Guanidine and Amidine Analogues of 3-[(2-aminoethylthio]-cyclosporin A
Example A
3-[(2-Guanidyl)-ethylthio]-cyclosporin A (III)
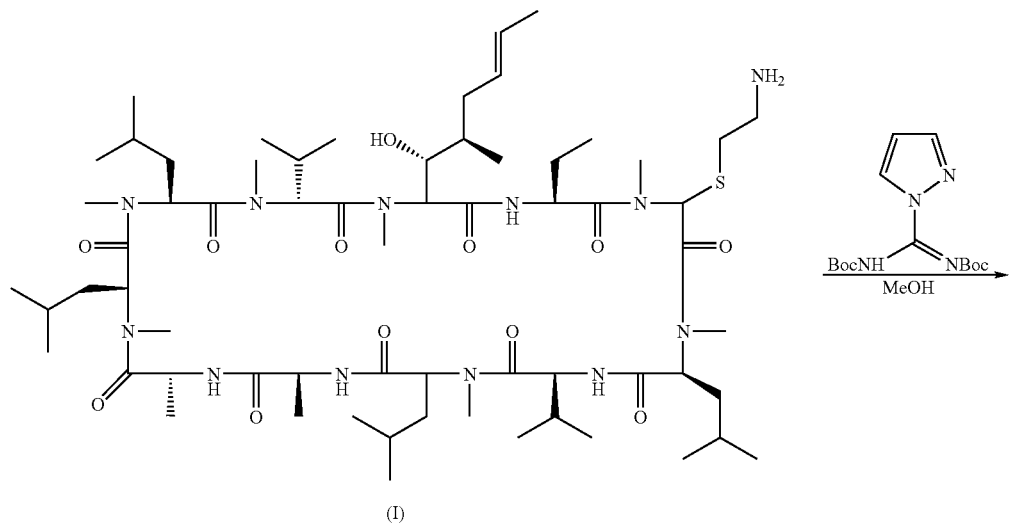
(I)
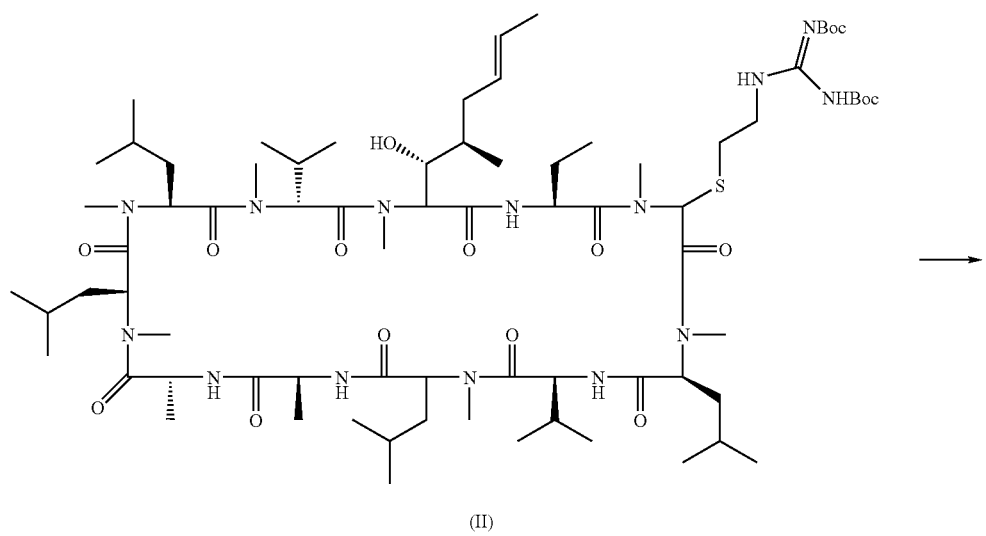
(II)

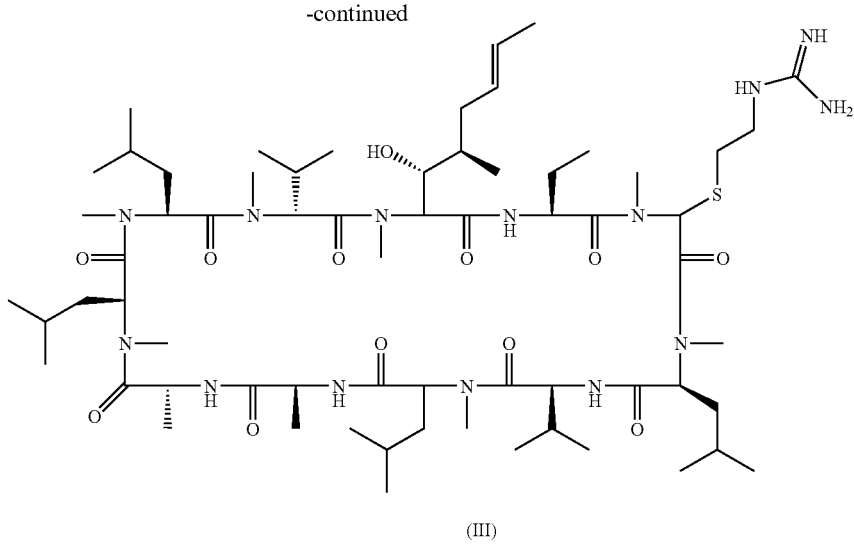

(III)

To a solution of 3-[(2-aminoethylthio]-cyclosporin A*-(I)) (200 mg, 0.16 mmol) in methanol (20 mL) was added di-tBoc-pyrazole carboxamidine (250 mg, 0.8 mmol), and the reagents were stirred together for 18 h. After this time, a further portion of the di-Tt-pyrazole carboxamidine (100 mg, 0.32 mmol) was added and the reaction was stirred for a further 3 h. The reaction was then reduced in vacuo, redissolved in dichloromethane, washed with 0.5M citric acid, and the organic layer was dried over $MgSO_4$ and reduced in vacuo. The product was then purified by chromatography column on a 10 g SPE cartridge eluting with diethyl ether to isolate 90 mg (40%) of desired product (II).

As the first member of the Guanidine and Amidine examples synthesized and because of the difficulties anticipated in characterising the final product (III), it was decided to fully and extensively characterize the di-tBoc protected guanidine (II) at this stage and to then take this material onto the free guanidine (III) by acid hydrolysis. Subsequent analogues in this Guanidine and Amidine subclass made from 3-[(2-aminoethylthio]-cyclosporin A were then characterised principally by MS.

Compound (II) was analysed by $^1H$, $^{13}C$, DEPT NMR and subsequently by a series of 2-D NMR experiments, HMQC, HMBC and DEPT-HMQC.

Presence of the 3-[(2-Guanidyl)-ethylthio] side chain was confirmed by 1D & 2D NMR. Analysis was performed in $CDCl_3$ solution at 300K on a Bruker DRX500 spectrometer.

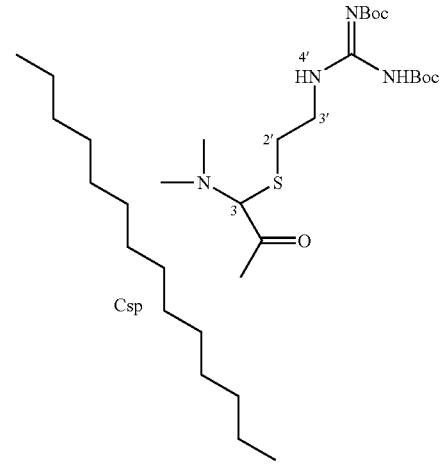

$^1H$ NMR Key Resonances:

δ=1.50, 1.51 ppm (2 singlets, 2×Boc, 18H, 6×CH3)

δ=5.89 ppm, (singlet, sarcosine, 1H)

2D Spectra

Using $^1H$ detected Heteronuclear Multiple Quantum Coherence (HMQC), Heteronuclear Multiple Bond Correlation (HMBC) and edited Heteronuclear Single Quantum Coherence (DEPT-HSQC) experiments, connectivity and assignment may be made confirming the presence of the 3-[(2-Guanidyl)-ethylthio] side chain.

H (3) to 2' (multiplet, $^1H$ 2.84 ppm, 2H).

2' to 3' (multiplet, $^1H$ 3.67 ppm, 2H).

3' to NH 4' (triplet $J_{HH}$ 5.8 Hz, $^1H$ 8.67 ppm, 1H).

To a solution of the di-tBoc protected 3-[(2-Guanidyl)-ethylthio]-cyclosporin A (II) (21 mg, 0.0138 mmol) in dichloromethane (0.3 mL) was added trifluoroacetic acid (0.3 mL) and the solution was stirred at room temperature for 1 hour. The solution was concentrated to give the product (III) as a white solid (20 mg; 100%).

Analysis by MS ($E^+$) showed a mass of 1320.2 (M+H) consistent with the proposed structure.

Example B

3-[(2-N,N-dimethylformamidinyl)-1-thioethyl]-cyclosporin A (III)

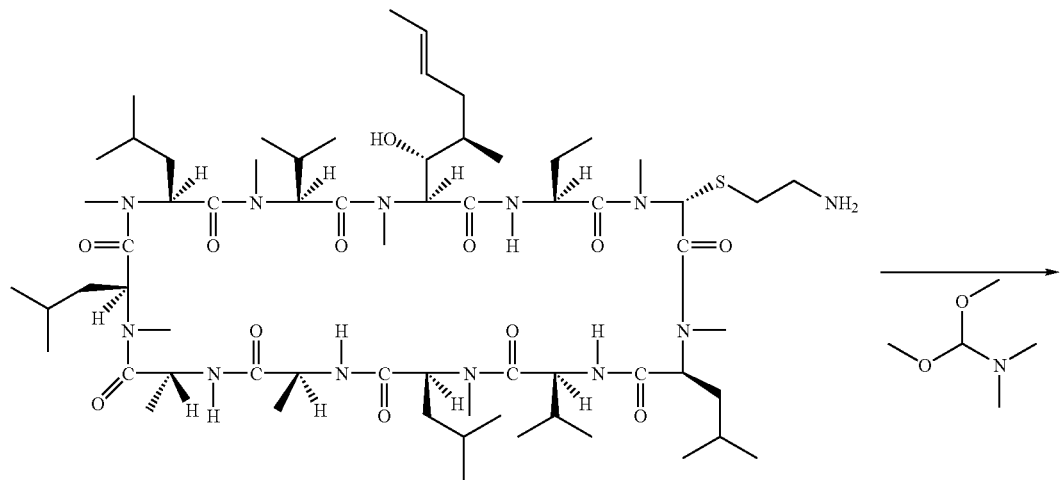

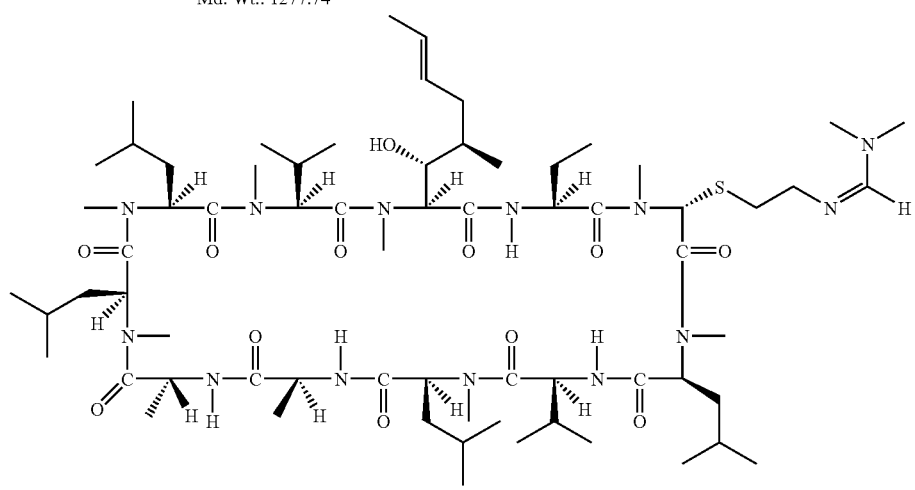

A mixed solution of 3-(1-thioethylamine)cyclosporine A (0.64 g, 0.5 mmol) and N,N-dimethylformamide dimethyl acetal in 20 mL of THF was refluxed for two hours. After removal of solvent under vacuum, the residue was subject to silica gel column using methylene/methanol (10:1) as eluents, 300 mg of pure product was obtained (yield: 45.0%).

MS (E+) showed a mass of 1332.82 (M+H$^+$) consistent with the proposed structure.

Other methods will be apparent to a chemist skilled in the art as will methods for preparing starting materials and intermediates etc.

In accordance with the present invention, the cyclosporin A derivatives may be applied, e.g. to an affected eye, in any efficacious concentration. When said cyclosporin A derivatives are applied to the eye as a topical ophthalmic composition the composition may comprise, 0.01 to saturation (e.g. greater than 20 weight percent) of said cyclosporin A derivative in a pharmaceutically acceptable excipient. From 0.01 to 50 weight percent, preferably from 0.1 to 20 weight percent, of cyclosporin A derivatives in a pharmaceutically acceptable excipient may be used. Such pharmaceutically acceptable excipients are, for example, animal oil, vegetable oil, an appropriate organic or aqueous solvent, an artificial tear solution, a natural or synthetic polymer, or an appropriate membrane to encapsulate the cyclosporin A derivative.

Specific examples of these pharmaceutically acceptable excipients are olive oil, arachis oil, castor oil, mineral oil, petroleum jelly, dimethyl sulphoxide, cremophor, Miglyol 182 (commercially available from Dynamit Nobel Kay-Fries Chemical Company, Mont Vale, N.J.), an alcohol (e.g. ethanol, n-propyl alcohol, or iso-propyl alcohol), liposomes or liposome-like products or a silicone fluid. Preferred excipients are dimethyl sulphoxide and olive oil. Mixtures of at least two of any suitable excipients may be used.

Examples of artificial tear excipients which can be advantageously used in the practice of this invention are isotonic sodium chloride, cellulose ethers such as hydroxypropylmethylcellulose and hydroxyethylcellulose, polyvinyl alcohol and available artificial tea solutions.

An example of a useful polymeric excipient is a polyoxyethylated castor oil.

Examples of pharmaceutically acceptable membranes which can be advantageously used in the practice of this invention are microdrone, an artificial lipid membrane, polyvinyl alcohol, or methylcellulose.

The cyclosporin A derivatives are advantageously administered topically as an ophthalmic drop (solution or suspension) or ophthalmic ointment containing an effective amount of the derivative. Concentrations of 0.01 to 50 weight percent, preferably 0.1 to 20 weight percent, of the cyclosporin A derivatives are used in the practice of the present invention.

In accordance with a method of the present invention, at least one of the cyclosporin A derivatives is administered topically in any quantity required to provide the degree of treatment needed. For example, 5 microliters to 1 milliliter of a solution, suspension, or ointment containing an effective amount of the cyclosporin A derivative, such as 0.01 to 50 weight percent, preferably 0.1 to 20 weight percent, of the cyclosporin A derivative is advantageously used.

Numerous advantages accrue with the practice of the present invention. The method of the present invention is useful in that it can locally prevent activation of a presystemic response. Topical administration of the cyclosporin A derivatives to a patient's tear deficient eye increases tear production in the eye. Thus, such treatment further serves to correct corneal and conjunctival disorders exacerbated by tear deficiency and KCS, such as corneal scarring, corneal ulceration, inflammation of the cornea or conjunctiva, filamentary keratitis, mucopurulent discharge and vascularization of the cornea. Furthermore, the cyclosporin A derivatives directly decrease the immune response and granulation and neovascularization.

Example 1

This example compares the relative potency of the cyclosporine analogues utilized in the method of the present invention with cyclosporine A in modulating Jurkat T cell functions.

A. Inhibition of T Cell Proliferation.

In this experiment the % Viable cells @ 10 uM for 48 hours is determined by WST Assay (Water Soluble Tetrazolium).

| Compound | % Viable cells |
|---|---|
| Cyclosporin A | 57 |
| CsA-A1 | 45 |
| CsA-A2 | 62 |
| CsA-A3 | 72 |
| CsA-A4 | 65 |
| CsA-A5 | 78 |
| CsA-A6 | 94 |

The results of this experiment shows that the cyclosporine analogues utilized in the method of the present invention are as good or better than cyclosporine A.

B. Induction of T Cell Apoptosis

The percentage (%) of apoptotic T cells is determined @ 10 uM compound concentration for 24 hours of incubation period.

| Cyclosporin A | 51 |
|---|---|
| CsA-A1 | 62 |
| CsA-A2 | 31 |
| CsA-A3 | 18 |
| CsA-A4 | 34 |
| CsA-A5 | 25 |
| CsA-A6 | 14 |

Again, the compound CsA-A1 shows surprisingly greater effect than cyclosporine A.

C. Suppression of IL-2 Production by T Cells

The percentage (%) inhibition in IL-2 production is determined @ 10 uM compound concentration for 24 hours of incubation period.

| Cyclosporin A | 100 |
|---|---|
| CsA-A1 | 100 |
| CsA-A2 | 82 |
| CsA-A3 | 28 |
| CsA-A4 | 19 |
| CsA-A5 | 36 |
| CsA-A6 | 4 |

The compound CsA-A1, surprisingly, shows equivalent effectiveness as compared to cyclosporine A in this experiment.

As a result of the experiments described in Example 1, CsA-A1 was selected for further work.

Example 2

This example compares the relative potency of CsA-A1, the most preferred cyclosporine A derivative utilized in the method of the present invention with cyclosporine A in an in-vivo modal of ocular inflammation.

A. Rat EIU Model: Acute Intraocular Inflammation

Rats were injected in the foot pad LPS (100 ug/rat.) 5 rats were treated in each of the following groups. The topical vehicle was the Restasis vehicle.

The systemic vehicle was:

| Ethanol (200 Proof) | 15% |
|---|---|
| Cremaphor EL | 15% |
| Polysorbate 80 | 2% |
| Water | 68% |

| Topically (t.i.d.) | Systemically (i.p., b.i.d) |
|---|---|
| Vehicle | 25 mg/kg Cyclosporin A (ethanol) |
| 0.05% Cyclosporin | 25/mg/kg CsA-A1 (ethanol) |
| 0.05% CsA-A1 | |

Samples of the blood and aqueous humor were collected and analyzed 24 hours post LPS injection. The histology of the cells was also recorded. The results are shown in FIG. 1.A. As can be observed in FIGS. 1A through E CsA-A1 showed a similar potency to cyclosporine A in inhibiting acute intraocular inflammation when applied topically and/or systemically in this experiment.

This example compares the relative potency of CsA-A1, the most preferred cyclosporine A derivative utilized in the method of the present invention with cyclosporine A in an in-vivo modal of ocular inflammation.

B. Rat EAU Model: Chronic Intraocular Inflammation

Rats were immunized with R16 (RIBP immunogenic peptide, 100 ug/rat. The rats were then fitted with Alzet Pump to deliver 5 mg/kg/day of the test sample, below, or injected intraperitoneal with 10 mg/kg, q.d. of the test sample. 5 rats were treated in each of the following groups. The vehicle was

| | | |
|---|---|---|
| | Ethanol (200 Proof) | 15% |
| | Cremaphor EL | 15% |
| | Polysorbate 80 | 2% |
| | Water | 68% |

In vivo fluorophotometry was performed on days 9, 12 and 14 post immunization. Aqueous samples and globes were collected and analyzed on day 14.

The results are shown in FIG. 2. as can be observed in FIGS. 2A through 2K E CsA-A1 showed a similar potency to cyclosporine A in inhibiting acute intraocular inflammation when applied by intraperitoneal injection in this experiment. However, as a result of its lower solubility in the vehicle, it appeared to be less effective when applied by the Alzet Pump.

The Rat EAU model is indicative of autoimmune-mediated inflammatory conditions. Indeed, uveitis may precede, accompany or develop following the onset of many systemic autoimmune diseases including juvenile rheumatoid arthritis (RA), psoriatic arthritis, multiple sclerosis (MS), inflammatory bowel disease and systemic lupus erythematosus. The etiology of these chronic inflammatory conditions is not well understood; however, evidence suggests that autoreactive T cells and antibodies recognizing self-antigens localized within affected tissues drives the chronic inflammatory response, e.g. uveal and/or retinal antigens, myelin proteins within central nervous system or components of cartilage in patients with uveitis, MS and RA respectively. In any case, environmental factors (e.g. viral or bacterial infection) in the context of a genetic predisposition (e.g. mutations in genes encoding HLA) are thought to break self-tolerance and trigger the onset of disease. This concept is exemplified in EAU and other models of autoimmune-mediated disease. Lewis rats immunized with uveal or retinal antigens, including S-antigen or interphotoreceptor retinoid binding protein (IRBP), exhibit similar clinical and histological disease profiles compared to patients with posterior uveitis. Genetically susceptible strains of mice immunized with type II collagen show histopathological and clinical similarities to patients with rheumatoid arthritis. Likewise, immunization with myelin peptides mimics the immunopathogenesis of MS, including myelin loss within white matter tracts of the CNS and paralysis, and these mice may also develop uveitis.

Further objects of this invention, together with additional features contributing thereto and advantages accruing therefrom will be apparent from the following examples of the invention.

The foregoing description details specific methods and compositions that can be employed to practice the present invention, and represents the best mode contemplated. Thus, however detailed the foregoing may appear in text, it should not be construed as limiting the overall scope hereof; rather, the ambit of the present invention was to be governed only by the lawful construction of the appended claims. In particular, although the method of the present invention has been described with the use of the specific cyclosporine A derivatives of the above formula, the novel cyclosporine derivatives that may be used in the method of the present invention further include 3-substituted iminoalkylthio cyclosporin A derivatives, preferably 3-substituted diaminoiminoalkylthio cyclosporin A derivatives, e.g. ((R)-(diamino)iminoalkylthio-Sar)$^3$-(4'-hydroxy-MeLeu)$^4$ cyclosporin A, ((R)-(alkyl)(dialkylamino)iminoalkylthio-Sar)$^3$-(4'-hydroxy-MeLeu)$^4$-cyclosporin A, ((R)-(alkyl)(dialkylamino)iminoalkylthio-Sar)$^3$-cyclosporin A derivatives and ((R)-(diamino)iminoalkylthio-Sar)$^3$-cyclosporin A derivatives.

The invention may be summarized as follows.

1. A method for the treatment of an inflammatory disease, disorder or condition of a mammal, comprising the step of administering to a patient in need thereof, a therapeutically effective amount of a cyclosporin A derivative selected from the group consisting of compounds represented by the formula:

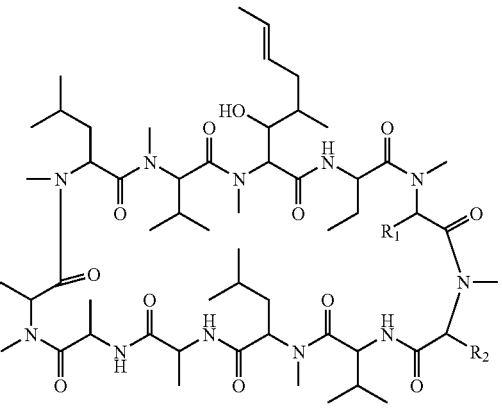

wherein $R_1$ is S-Alk-R wherein Alk is an alkylene linkage and R is a hydrogen or a unsubstituted or substituted hydrocarbyl group.

2. The method of 1 wherein Alk is a methylene or a $C_3$ to $C_6$ alkenylenyl linkage.

3. The method of 1 wherein $R_1$ is a methylene or a $C_2$ to $C_6$ polymethylene linkage.

4. The method of 1 wherein $R_1$ is a $C_3$ to $C_6$ alkenylenyl linkage.

5. The method of 1 wherein R is —N=C(NR$_3$R$_4$)(NR$_5$R$_6$) or —NR$_7$C(NR$_3$)(C=NR$_5$), wherein R$_3$-R$_7$ is H, Alk, Ar or (CH$_2$)nAr wherein Ar is an aryl group and n is an integer of from 1 to 13 or R$_3$ and R$_4$ or R$_4$ and R$_5$ or R$_5$ and R$_7$ or R$_3$ and R$_7$, together may be —CH$_2$—CH$_2$— or —CH$_2$—CH$_2$—CH$_2$—.

6. The method of 1 wherein said cyclosporine A derivative is a 3-substituted diaminoiminoalkylthio cyclosporine A derivative.

7. The method of 1 wherein said cyclosporine A derivative is selected from the group consisting of ((R)-(diamino)iminoalkylthio-Sar)$^3$-(4'-hydroxy-MeLeu)$^4$ cyclosporin A derivatives, ((R)-(alkyl)(dialkylamino)iminoalkylthio-Sar)$^3$-(4'-hydroxy-MeLeu)$^4$-cyclosporin A, ((R)-(alkyl)(dialkylamino)iminoalkylthio-Sar)$^3$-cyclosporin A derivatives and ((R)-(diamino)iminoalkylthio-Sar)$^3$-cyclosporin A derivatives.

8. The method of 1 wherein said cyclosporine A derivative is selected from the group of compounds according to 1 wherein $R_1$ is —S(CH$_2$)$_2$N=C(NH$_2$)$_2$ and $R_2$ is —CH$_2$CH(CH$_3$)$_2$, —CH$_2$C(OH)(CH$_3$)$_2$, —CH(CH$_3$)$_2$ or —CH(CH$_3$)CH$_2$CH$_3$.

9. The method of 1 wherein the compound is administered in a composition comprising 0.1 to 20 wt % of the compound together with a pharmaceutically acceptable excipient.

10. The method of 9 wherein the pharmaceutically acceptable excipient is selected from the group consisting of animal oil and vegetable oil.

11. The method of 9 wherein the pharmaceutically acceptable excipient is selected from the group consisting of olive oil, arachis oil, castor oil, mineral oil, petroleum jelly, dimethyl sulphoxide, an alcohol, silicone fluid and mixtures thereof 12. The method of 1 wherein $R_1$ is a hydrogen atom or a radical of formula (Ia):

in which

Alk-$R_{11}$ represents a methyl radical, or alternatively

Alk represents a C$_2$-C$_6$ straight chain or branched alkylene radical or a C$_3$-C$_6$ cycloalkylene radical, and $R_{11}$ represents a hydrogen atom or a hydroxyl, carboxyl or alkyloxycarbonyl radical, or an —NR$_{12}$R$_{13}$ radical in which R$_{12}$ and R$_{13}$, which are identical or different, represent a hydrogen atom or a phenyl, alkyl, C$_2$-C$_4$ alkenyl or C$_3$-C$_6$ cycloalkyl radical, said radical optionally substituted with selected from a halogen atom, an alkyloxy, alkyloxycarbonyl, amino, alkylamino and dialkylamino radical; or R$_{12}$ and R$_{13}$ represent a benzyl or saturated or unsaturated heterocycyclic radical, said heterocycylic radical containing from 5 to 6 ring members and from 1 to 3 heteroatoms;

or in which R$_{12}$ and R$_{13}$ form, together with the nitrogen atom to which they are attached, a saturated or unsaturated 4- to 6-membered heterocycle, which heterocycle having an additional heteroatom selected from nitrogen, oxygen and sulphur, and wherein said saturated or unsaturated heterocycle is optionally substituted by an alkyl, phenyl or benzyl radical, or $R_1$ is a radical of the formula (Ib): —N(R$_{14}$)—(CH$_2$)$_n$—NR$_{12}$R$_{13}$ in which R$_{12}$ and R$_{13}$ are as defined above, R$_{14}$ represents a hydrogen atom or an alkyl radical and n is an integer ranging from 2 to 4, and $R_2$ is selected from the group consisting of hydroxyl, lower alkyl and hydroxyl substituted lower alkyl, with the proviso that, when $R_1$ is a hydrogen atom, then $R_2$ is not an alkyl butyl? radical, and wherein the alkyl portions or radicals defined above are straight chain or branched and contain from 1 to 4 carbon atoms, or a pharmaceutically acceptable salt thereof.

13. The method of 12 wherein in the cyclosporine A derivatives of the formula, the trans butene moiety, which is normally present in the 1-position of cyclosporine A, is replaced with R$_{15}$ wherein R$_{15}$ represents a radical of formula —CH$_2$CHCHCH$_2$—R$_{16}$ (Ic) or —CH$_2$SR$_{17}$ (Id), wherein R$_{16}$ represents an alkylthio, aminoalkylthio, alkylaminoalkylthio, dialkylaminoalkylthio, pyrimidinylthio, thiazolylthio, N-alkylimidazolylthio, hydroxyalkylphenylthio, hydroxyalkylphenyloxy, nitrophenylamino or 2-oxopyrimidin-1-yl radical and R$_{17}$ represents an alkyl radical.

14. The method of 12 wherein R represents
a hydroxyl radical,
a carboxyl radical,
an alkyloxycarbonyl radical,
an —NR$_{12}$R$_{13}$ radical in which R$_{12}$ and R$_{13}$, which are identical or different, represent a hydrogen atom or an alkyl, C$_2$-C$_4$ alkenyl, C$_3$-C$_6$ cycloalkyl or optionally substituted phenyl radical, wherein said phenyl radical may be substituted by a halogen atom, or an alkyloxy, alkyloxycarbonyl, amino, alkylamino or dialkylamino radical, or represent a benzyl or heterocyclyl radical, wherein said heterocyclyl radical may be saturated or unsaturated and contains 5 or 6 ring members and from 1 to 3 heteroatoms; or in which R$_{12}$ and R$_{13}$ form, together with the nitrogen atom to which they are attached, a saturated or unsaturated heterocycle containing 4 to 6 ring members, which heterocycle may optionally contain an additional heteroatom selected from nitrogen, oxygen and sulphur, and wherein said saturated or unsaturated heterocycle is optionally substituted by an alkyl, phenyl or benzyl radical, or a radical of the formula —N(R$_{14}$)—(CH$_2$)$_n$—NR$_{12}$R$_{13}$ in which R$_{12}$ and R$_{13}$ are as defined above R$_{14}$ represents a hydrogen atom or an alkyl radical, and n is an integer from 2 to 4;

wherein the alkyl portions or radicals defined above are straight chain or branched and contain from 1 to 4 carbon atoms;

or a pharmaceutically acceptable salt thereof

15. The method of 14, wherein:
Alk represents a C$_3$-C$_6$ straight chain or branched alkylene radical, and
R represents
a hydroxyl radical, or
an —NR$_{12}$R$_{13}$ radical in which R$_{12}$ and R$_{13}$, which are identical or different, represent a hydrogen atom or an alkyl, C$_{3-4}$ alkenyl or optionally substituted phenyl radical, wherein said phenyl radical may be substituted by a halogen atom or an alkyloxy, alkyloxycarbonyl, amino, alkylamino or dialkylamino radical, or represents a benzyl radical; or in which R$_{12}$ and R$_{13}$ form, together with the nitrogen atom to which they are attached, a saturated or unsaturated heterocycle containing 4 to 6 ring members, which heterocycle may optionally contain an additional heteroatom selected from nitrogen, oxygen and sulphur, and wherein said saturated or unsaturated heterocycle is optionally substituted by an alkyl radical;

or a pharmaceutically acceptable salt thereof

16. The method of 14, wherein:
Alk represents a C$_{2-6}$ straight chain or branched alkylene radical, and
R represents a hydroxyl radical, or an —NR$_{12}$R$_{13}$ radical in which R$_{12}$ and R$_{13}$, which are identical or different, represent a hydrogen atom or an alkyl, allyl, phenyl or benzyl radical; or in which R$_{12}$ and R$_{13}$ form, together with the nitrogen atom to which they are attached, a heterocycle selected from azetidinyl, piperidyl, piperazinyl, N-methylpiperazinyl, N-phenylpiperazinyl, N-benzylpiperazinyl, morpholino, tetrahydropyridyl, methyltetrahydropyridyl and phenyltetrahydropyridyl;

or a pharmaceutically acceptable salt thereof

17. The method of 16, wherein the cyclosporine A derivative is selected from the group consisting of [(R)-2-(N,N-dimethyl-amino)ethylthio-Sar]$^3$-[4'-hydroxy-MeLeu]$^4$-cyclosporin A,

[(R)-2-(1-piperidyl)-ethylthio-Sar]$^3$-[4'-hydroxy-MeLeu]$^4$-cyclosporin A,

[(R)-2-(N-methyl-N-t-butylamino)ethylthio-Sar]$^3$-[4'-hydroxy-MeLeu]$^4$-cyclosporin A,

[(R)-2-(hydroxy)-ethylthio-Sar]$^3$-[4'-hydroxy-MeLeu]$^4$-cyclosporin A,

[(R)-2-(N,N-diethyl-amino)ethylthio-Sar]$^3$-[4'-hydroxy-MeLeu]$^4$-cyclosporin A,

[(R)-2-(N,N-dimethylamino)ethylthio-Sar]$^3$-cyclosporin A,

[(R)-2-(1-piperidyl)ethylthio-Sar]$^3$-cyclosporin A,

[(R)-2-(N-methyl-N-1-propylamino)ethylthio-Sar]$^3$-cyclosporin A and
[(R)-2-(N-methyl-N-t-butylamino)ethylthio-Sar]$^3$-cyclosporin A, and pharmaceutically acceptable salts thereof.

18. The method of 16, wherein the cyclosporine A derivative is (R)-(diethylaminoethylthio-Sar)$^3$ cyclosporin A.

19. A method of treating inflammatory diseases selected from the group consisting of ocular inflammatory diseases, dermal inflammatory diseases, inflammatory rheumatic diseases, inflammatory bowel disease, neuroinflammatory diseases and autoimmune hematological diseases and disorders wherein said cyclosporine A derivative is selected from the group consisting of compounds represented by the formula:

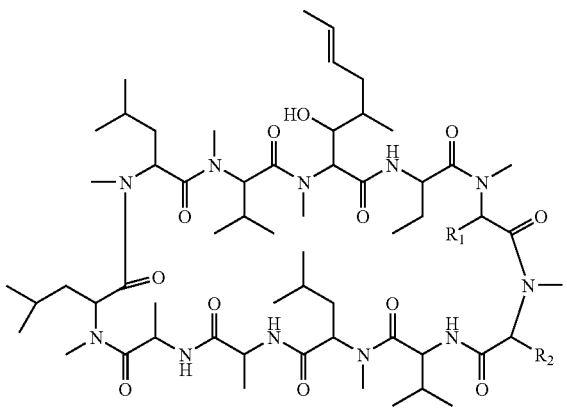

wherein $R_1$ is S-Alk-R wherein Alk is an alkylene or alkylenyl linkage, R is
—N=C(NR$_3$R$_4$)(NR$_5$R$_6$) or —NR$_7$-[(NR$_3$R$_4$)C=NR$_5$], or —N=C(R$_8$)(NR$_9$R$_{10}$), wherein R$_3$-R$_7$ is H, Alk, Ar or (CH$_2$)nAr wherein Ar is an aryl group and n is an integer of from 1 to 13 or R$_3$ and R$_4$, or R$_4$ and R$_5$, or R$_5$ and R$_7$, or R$_3$ and R$_7$, or R$_9$ and R$_{10}$, or R$_8$ and R$_9$, together, may be —(CH$_2$)$_x$—, wherein x is an integer of from 2 to 5 and R$_2$ is selected from the group consisting of hydroxyl, lower alkyl and hydroxyl-substituted lower alkyl.

20. The method of 19 wherein $R_1$ is a methylene or a $C_2$ to $C_6$ polymethylene linkage.

21. The method of 19 wherein $R_1$ is a $C_3$ to $C_6$ alkenylenyl linkage.

22. The method of 19 wherein R is —N=C(NR$_3$R$_4$)(NR$_5$R$_6$) or —NR$_7$C(NR$_3$)(C=NR$_5$), wherein R$_3$-R$_7$ is H, Alk, Ar or (CH$_2$)nAr wherein Ar is an aryl group and n is an integer of from 1 to 13 or R$_3$ and R$_4$ or R$_4$ and R$_5$ or R$_5$ and R$_7$ or R$_3$ and R$_7$, together may be —CH$_2$—CH$_2$— or —CH$_2$—CH$_2$—CH$_2$—.

23. The method of 19 wherein said cyclosporine A derivative is a 3-substituted diaminoiminoalkylthio cyclosporine A derivative.

24. The method of 19 wherein said cyclosporine A derivative is selected from the group consisting of ((R)-(diamino)iminoalkyllthio-Sar)$^3$-(4'-hydroxy-MeLeu)$^4$ cyclosporin A derivatives, ((R)-(alkyl)(dialkylamino)iminoalkylthio-Sar)$^3$-(4'-hydroxy-MeLeu)$^4$-cyclosporin A, ((R)-(alkyl)(dialkylamino)iminoalkylthio-Sar)$^3$-cyclosporin A derivatives and ((R)-(diamino)iminoalkylthio-Sar)$^3$-cyclosporin A derivatives.

25. The method of 19 wherein $R_1$ is a hydrogen atom or a radical of formula (Ia):

—S-Alk-R$_{11}$  (Ia)

in which
Alk-R$_{11}$ represents a methyl radical, or alternatively
Alk represents a $C_2$-$C_6$ straight chain or branched alkylene radical or a $C_3$-$C_6$ cycloalkylene radical, and
R$_{11}$. represents
a hydrogen atom or a hydroxyl, carboxyl or alkyloxycarbonyl radical, or
an —NR$_{12}$R$_{13}$ radical in which R$_{12}$ and R$_{13}$, which are identical or different, represent a hydrogen atom or a phenyl, alkyl, $C_2$-$C_4$ alkenyl or $C_3$-$C_6$ cycloalkyl radical, said radical optionally substituted with selected from a halogen atom, an alkyloxy, alkyloxycarbonyl, amino, alkylamino and dialkylamino radical; or
R$_{12}$ and R$_{13}$ represent a benzyl or saturated or unsaturated heterocycylic radical, said heterocycylic radical containing from 5 to 6 ring members and from 1 to 3 heteroatoms;
or in which R$_{12}$ and R$_{13}$ form, together with the nitrogen atom to which they are attached, a saturated or unsaturated 4- to 6-membered heterocycle, which heterocycle having an additional heteroatom selected from nitrogen, oxygen and sulphur, and wherein said saturated or unsaturated heterocycle is optionally substituted by an alkyl, phenyl or benzyl radical, or
$R_1$ is a radical of the formula (Ib): —N(R$_{14}$)—(CH$_2$)$_n$—NR$_{12}$R$_{13}$ in which R$_{12}$ and R$_{13}$ are as defined above, R$_{14}$ represents a hydrogen atom or an alkyl radical and n is an integer ranging from 2 to 4,
and R$_2$ is selected from the group consisting of hydroxyl, lower alkyl and hydroxyl substituted lower alkyl,
with the proviso that, when $R_1$ is a hydrogen atom, then R$_2$ is not an alkyl butyl radical, and wherein the alkyl portions or radicals defined above are straight chain or branched and contain from 1 to 4 carbon atoms, or a pharmaceutically acceptable salt thereof.

26. The method of 25 wherein in the cyclosporine A derivatives of the formula, the trans butene moiety, which is normally present in the 1-position of cyclosporine A, is replaced with R$_{15}$ wherein R$_{15}$ represents a radical of formula
—CH$_2$CHCHCH$_2$—R$_{16}$ (Ic) or —CH$_2$SR$_{17}$ (Id), wherein R$_{16}$ represents an alkylthio, aminoalkylthio, alkylaminoalkylthio, dialkylaminoalkylthio, pyrimidinylthio, thiazolylthio, N-alkylimidazolylthio, hydroxyalkylphenylthio, hydroxyalkylphenyloxy, nitrophenylamino or 2-oxopyrimidin-1-yl radical and R$_{17}$ represents an alkyl radical.

27. The method of 25 wherein R represents
a hydroxyl radical,
a carboxyl radical,
an alkyloxycarbonyl radical,
an —NR$_{12}$R$_{13}$ radical in which R$_{12}$ and R$_{13}$, which are identical or different, represent a hydrogen atom or an alkyl, $C_2$-$C_4$ alkenyl, $C_3$-$C_6$ cycloalkyl or optionally substituted phenyl radical, wherein said phenyl radical may be substituted by a halogen atom, or an alkyloxy, alkyloxycarbonyl, amino, alkylamino or dialkylamino radical, or represent a benzyl or heterocyclyl radical, wherein said heterocyclyl radical may be saturated or unsaturated and contains 5 or 6 ring members and from 1 to 3 heteroatoms; or in which R$_{12}$ and R$_{13}$ form, together with the nitrogen atom to which they are attached, a saturated or unsaturated heterocycle containing 4 to 6 ring members, which heterocycle may optionally contain an additional heteroatom selected from nitrogen, oxygen and sulphur, and wherein said saturated or unsaturated heterocycle is optionally substituted by an alkyl, phenyl or benzyl radical, or
a radical of the formula —N(R$_{14}$)—(CH$_2$)$_n$—NR$_{12}$R$_{13}$ in which R$_{12}$ and R$_{13}$ are as defined above R$_{14}$ represents a hydrogen atom or an alkyl radical, and n is an integer from 2 to 4;

wherein the alkyl portions or radicals defined above are straight chain or branched and contain from 1 to 4 carbon atoms;
or a pharmaceutically acceptable salt thereof.

28. The method of 27, wherein:
Alk represents a $C_3$-$C_6$ straight chain or branched alkylene radical, and
R represents a hydroxyl radical, or an —$NR_{12}R_{13}$ radical in which $R_{12}$ and $R_{13}$, which are identical or different, represent a hydrogen atom or an alkyl, $C_{3-4}$ alkenyl or optionally substituted phenyl radical, wherein said phenyl radical may be substituted by a halogen atom or an alkyloxy, alkyloxycarbonyl, amino, alkylamino or dialkylamino radical, or represents a benzyl radical; or in which $R_{12}$ and $R_{13}$ form, together with the nitrogen atom to which they are attached, a saturated or unsaturated heterocycle containing 4 to 6 ring members, which heterocycle may optionally contain an additional heteroatom selected from nitrogen, oxygen and sulphur, and wherein said saturated or unsaturated heterocycle is optionally substituted by an alkyl radical;
or a pharmaceutically acceptable salt thereof.

29. The method of 27, wherein:
Alk represents a $C_{2-6}$ straight chain or branched alkylene radical, and
R represents a hydroxyl radical, or an —$NR_{12}R_{13}$ radical in which $R_{12}$ and $R_{13}$, which are identical or different, represent a hydrogen atom or an alkyl, allyl, phenyl or benzyl radical; or in which $R_{12}$ and $R_{13}$ form, together with the nitrogen atom to which they are attached, a heterocycle selected from azetidinyl, piperidyl, piperazinyl, N-methylpiperazinyl, N-phenylpiperazinyl, N-benzylpiperazinyl, morpholino, tetrahydropyridyl, methyltetrahydropyridyl and phenyltetrahydropyridyl;
or a pharmaceutically acceptable salt thereof.

30. The method of 29, wherein the cyclosporine A derivative is selected from the group consisting of
[(R)-2-(N,N-dimethyl-amino)ethylthio-Sar]$^3$-[4'-hydroxy-MeLeu]$^4$-cyclosporin A,
[(R)-2-(1-piperidyl)-ethylthio-Sar]$^3$-[4'-hydroxy-MeLeu]$^4$-cyclosporin A,
[(R)-2-(N-methyl-N-t-butylamino)ethylthio-Sar]$^3$-[4'-hydroxy-MeLeu]$^4$-cyclosporin A,
[(R)-2-(hydroxy)-ethylthio-Sar]$^3$-[4'-hydroxy-MeLeu]$^4$-cyclosporin A,
[(R)-2-(N,N-diethyl-amino)ethylthio-Sar]$^3$-[4'-hydroxy-MeLeu]$^4$-cyclosporin A,
[(R)-2-(N,N-dimethylamino)ethylthio-Sar]$^3$-cyclosporin A,
[(R)-2-(1-piperidyl)ethylthio-Sar]$^3$-cyclosporin A,
[(R)-2-(N-methyl-N-i-propylamino)ethylthio-Sar]$^3$-cyclosporin A and
[(R)-2-(N-methyl-N-t-butylamino)ethylthio-Sar]$^3$-cyclosporin A, and pharmaceutically acceptable salts thereof.

31. The method of 30, wherein the cyclosporine A derivative is (R)-(diethylaminoethylthio-Sar)$^3$ cyclosporin A.

32. The method of 19 wherein said ocular inflammatory disease is keratoconjunctivitis sicca, vernal keratoconjunctivitis, allergic conjunctivitis, or uveitis.

33. The method of 19 wherein said dermal inflammatory disease is psoriasis or atopic dermatitis.

34. The method of 19 wherein said inflammatory rheumatic disease is rheumatoid arthritis, scleroderma, systemic lupus erythematosus, Wegener granulamatosis, polymyositis, dermatomyositis, psoriatic arthritis, ankylosing spondylitis, Reiter's syndrome or juvenile rheumatoid arthritis.

35. The method of 19 wherein said ocular inflammatory bowel disease is ulcerative colitis or Crohn's disease.

36. The method of 19 wherein said neuroinflammatory disease is multiple sclerosis.

37. The method of 19 wherein said ocular autoimmune hematological disorder is hemolytic anaemia, aplastic anaemia, pure red cell anaemia, or idiopathic thrombocytopaenia.

What is claimed is:

1. A method for the treatment of an inflammatory condition of a mammal, comprising the step of administering to a patient in need thereof, a therapeutically effective amount of a cyclosporin A derivative represented by the following formula:

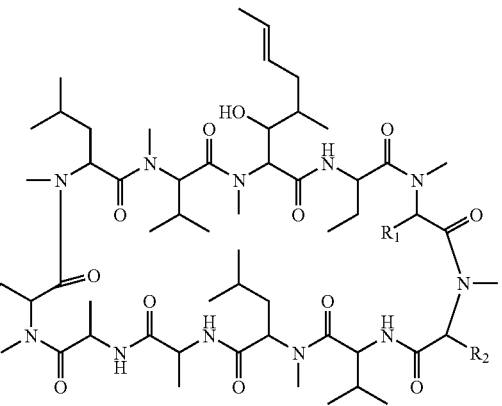

wherein $R_1$ is S-Alk-R wherein Alk is an alkylene linkage and, R is —N═C($NR_3R_4$)($NR_5R_6$), wherein $R_3$-$R_6$ is H, Alk, Ar or ($CH_2$)nAr wherein Ar is an aryl group and n is an integer of from 1 to 13 or $R_3$ and $R_4$ or $R_4$ and $R_5$, together may be —$CH_2$—$CH_2$— or —$CH_2$—$CH_2$—$CH_2$—, and $R_2$ is —$CH_2CH(CH_3)_2$, —$CH_2C(OH)(CH_3)_2$, —$CH(CH_3)_2$ or —$CH(CH_3)CH_2CH_3$.

2. The method of claim 1 wherein Alk is a methylene or a $C_3$ to $C_6$ alkenylenyl linkage.

3. The method of claim 1, wherein the inflammatory condition is selected from the group consisting of ocular inflammatory diseases, dermal inflammatory diseases, inflammatory rheumatic diseases, inflammatory bowel disease, neuroinflammatory diseases and autoimmune hematological diseases.

4. The method of claim 3 wherein said ocular inflammatory disease is keratoconjunctivitis sicca, vernal keratoconjunctivitis, allergic conjunctivitis, or uveitis.

5. The method of claim 3 wherein said dermal inflammatory disease is psoriasis or atopic dermatitis).

6. The method of claim 3 wherein said inflammatory rheumatic disease is rheumatoid arthritis, scleroderma, systemic lupus erythematosus, Wegener granulamatosis, polymyositis, dermatomyositis, psoriatic arthritis, ankylosing spondylitis, Reiter's syndrome or juvenile rheumatoid arthritis).

7. The method of claim 3 wherein said inflammatory bowel disease is ulcerative colitis or Crohn's disease.

8. The method of claim 3 wherein said neuroinflammatory disease is multiple sclerosis.

9. The method of claim 3 wherein said autoimmune hematological disorder is hemolytic anaemia, aplastic anaemia, pure red cell anaemia, or idiopathic thrombocytopaenia.

* * * * *

UNITED STATES PATENT AND TRADEMARK OFFICE
CERTIFICATE OF CORRECTION

PATENT NO. : 8,524,671 B2
APPLICATION NO. : 12/785133
DATED : September 3, 2013
INVENTOR(S) : Michael E. Garst et al.

Page 1 of 2

It is certified that error appears in the above-identified patent and that said Letters Patent is hereby corrected as shown below:

In the Specification

In column 4, line 3, delete "granulamatosis," and insert -- granulomatosis, --, therefor.

In column 4, line 33, delete "nucleocapside)." and insert -- nucleocapsid). --, therefor.

In column 22, line 52, delete "Cremaphor EL" and insert -- Cremophor EL --, therefor.

In column 23, line 17, delete "Cremaphor EL" and insert -- Cremophor EL --, therefor.

In column 25, line 14, delete "thereof" and insert -- thereof. --, therefor.

In column 25, line 33, delete "heterocycylic" and insert -- heterocyclic --, therefor.

In column 25, line 33, delete "heterocycylic" and insert -- heterocyclic --, therefor.

In column 25, line 48, delete "butyl?" and insert -- butyl --, therefor.

In column 26, line 22, delete "thereof" and insert -- thereof. --, therefor.

In column 26, line 40, delete "thereof" and insert -- thereof. --, therefor.

In column 26, line 53, delete "thereof" and insert -- thereof. --, therefor.

In column 27, line 1, delete "(N-methyl-N-1-propylamino)" and insert
-- (N-methyl-N-i-propylamino) --, therefor.

In column 28, line 15, delete "heterocycylic" and insert -- heterocyclic --, therefor.

In column 28, line 15, delete "heterocycylic" and insert -- heterocyclic --, therefor.

In column 29, line 63, delete "granulamatosis," and insert -- granulomatosis, --, therefor.

In the Claims

In column 30, line 34, in claim 1, delete "(CH$_2$)nAr" and insert -- (CH$_2$)nAr, --, therefor.

In column 30, line 51, in claim 5, delete "dermatitis)." and insert -- dermatitis. --, therefor.

Signed and Sealed this
Twenty-first Day of April, 2015

Michelle K. Lee
*Director of the United States Patent and Trademark Office*

In column 30, line 54, in claim 6, delete "granulamatosis," and insert -- granulomatosis, --, therefor.

In column 30, line 56, in claim 6, delete "arthritis)." and insert -- arthritis. --, therefor.